United States Patent
Tjarnehov et al.

(10) Patent No.: US 11,247,955 B2
(45) Date of Patent: Feb. 15, 2022

(54) PROCESS FOR THE PREPARATION OF METHANOL

(71) Applicant: Haldor Topsøe A/S, Kgs. Lyngby (DK)

(72) Inventors: Emil Andreas Tjarnehov, Limhamn (SE); Lars Storm Pedersen, Farum (DK); Michael Hultqvist, Bagsværd (DK); Søren Grønborg Eskesen, Espergærde (DK); Louise Wissing Jensen, Kgs. Lyngby (DK)

(73) Assignee: Haldor Topsoe A/S, Lyngby (DK)

( * ) Notice: Subject to any disclaimer, the term of this patent is extended or adjusted under 35 U.S.C. 154(b) by 0 days.

(21) Appl. No.: 17/269,607

(22) PCT Filed: Aug. 28, 2019

(86) PCT No.: PCT/EP2019/072965
§ 371 (c)(1),
(2) Date: Feb. 19, 2021

(87) PCT Pub. No.: WO2020/052979
PCT Pub. Date: Mar. 19, 2020

(65) Prior Publication Data
US 2021/0363079 A1    Nov. 25, 2021

(30) Foreign Application Priority Data
Sep. 13, 2018  (DK) .......................... PA 2018 00573

(51) Int. Cl.
| | | |
|---|---|---|
| *C07C 29/151* | (2006.01) | |
| *C07C 29/80* | (2006.01) | |
| *C07C 31/04* | (2006.01) | |
| *C25B 1/04* | (2021.01) | |
| *C07C 29/152* | (2006.01) | |

(52) U.S. Cl.
CPC ........ *C07C 29/1518* (2013.01); *C07C 29/152* (2013.01); *C07C 29/80* (2013.01); *C25B 1/04* (2013.01)

(58) Field of Classification Search
None
See application file for complete search history.

(56) References Cited

U.S. PATENT DOCUMENTS

| | | |
|---|---|---|
| 5,443,804 A | 8/1995 | Parker et al. |
| 2013/0214542 A1 | 8/2013 | Knop et al. |
| 2015/0353454 A1 | 12/2015 | Iijima |
| 2016/0237858 A1 | 8/2016 | Bergins et al. |
| 2017/0166503 A1 | 6/2017 | Grauer |
| 2017/0283724 A1 | 10/2017 | Bergins et al. |

FOREIGN PATENT DOCUMENTS

| | | |
|---|---|---|
| CN | 104725179 A | 6/2015 |
| CN | 106242946 A | 12/2016 |
| CN | 106748646 A | 5/2017 |
| EP | 1182185 A2 | 2/2002 |
| WO | WO 2013/029701 A1 | 3/2013 |
| WO | WO 2014/087433 A1 | 6/2014 |
| WO | WO 2018/019875 A1 | 2/2018 |

*Primary Examiner* — Medhanit W Bahta
(74) *Attorney, Agent, or Firm* — Blank Rome LLP

(57) ABSTRACT

Process for the preparation of a methanol product comprising the steps of a) providing a first process stream consisting essentially of carbon dioxide; b) providing a second process stream consisting of hydrogen by electrolyzing water in an electrolysis unit; c) mixing the first and second process in amount to obtain a methanol synthesis gas with a mole ratio of $H_2$ and $CO_2$ of between 2.5 and 3.5; d) catalytic converting the methanol synthesis gas into raw methanol in at least one methanol reactor; e) purifying the raw methanol in a distillation unit; and recovering waste heat generated in the electrolysis unit in step (b) by transferring the waste heat to a circulating heat transfer medium by indirect heat exchange with the waste heat and by indirect heat exchange of the heated heat transfer medium with steam used for the distillation of the raw methanol, wherein the heated transfer medium is compressed upstream the indirect heat exchange with steam.

4 Claims, No Drawings

PROCESS FOR THE PREPARATION OF METHANOL

The present application is directed to the preparation of methanol from a synthesis gas consisting of carbon dioxide and hydrogen. More particular, the invention utilize electrolysis of water for the preparation of hydrogen and carbon dioxide recovery from e.g off or flue gas, in the catalytic preparation of methanol according to reaction $$CO_2 + 3H_2 \rightarrow CH_3OH + H_2O$$

Hydrogen in MeOH production, normally provided in a synthesis gas generated by steam reforming. Hydrogen can also be produced by electrolysis of water and the product hydrogen is mixed with a carbon feedstock to produce methanol over a synthesis catalyst.

To generate the hydrogen by electrolysis requires a large amount of electricity and a part of the electricity is lost as waste heat due to the efficiency. The heat is typically removed by a cooling media and lost. To increase the overall efficiency of a plant where electrolysis is used the waste heat must to be utilized.

The problem when using waste heat from electrolysis is that the heat is recovered at a relatively low temperature in a heat transfer medium and must be increased in order to be useful for heat transfer in a process unit.

We found that when arranging a heat pump with a compressor in a heating loop with a circulating heat transfer medium and indirect heat exchangers, the low temperature heat can be increased in the heat transfer medium and is then useful in a in a process where low value heat is required.

In process of the invention, a heat pump is installed in a loop with circulating heat transfer medium to utilize the waste heat from the water electrolysis in the methanol distillation where steam is used. This will lower the requirement to steam produced.

Thus, this invention provides a process for the preparation of a methanol product comprising the steps of a) providing a first process stream consisting essentially of carbon dioxide;

b) providing a second process stream consisting of hydrogen by electrolyzing water in an electrolysis unit;

c) mixing the first and second process stream in amount to obtain a methanol synthesis gas with a mole ratio of H2 and CO2 of between 2.5 and 3.5;

d) catalytic converting the methanol synthesis gas into raw methanol in at least one methanol reactor;

e) purifying the raw methanol in a distillation unit; and
recovering waste heat generated in the electrolysis unit in step (b) by transferring the waste heat to a circulating heat transfer medium by indirect heat exchange with the waste heat and by indirect heat exchange of the heated heat transfer medium with steam used for the distillation of the raw methanol, wherein the heated transfer medium is compressed upstream the indirect heat exchange with steam.

An essential feature of the invention is a heating loop holding a circulating heat transfer medium and compressor, heat exchangers and a flash evaporation device.

Thereby the overall energy consumption in the process is reduced as the power required to operate the compressor is less than the power from heat utilized.

Suitable heat transfer media have a boiling point lower than the temperature in the waste heat transferred from the electrolysis unit at a given pressure downstream the flash evaporation and higher than the heating surface of the heat exchanger in the methanol distillation unit at the pressure at the discharge side of the compressor.

When operating the process according to the invention, the heat transfer medium, in its gaseous state, is pressurized and circulated through the loop by the compressor. On the discharge side of the compressor, the hot and pressurized vaporized heat transfer medium is cooled in a heat exchanger by heat exchange with steam used in the methanol distillation unit and condensed into a pressurized liquid. The condensed heat transfer medium is then flash evaporated through a pressure-lowering device e.g. an expansion valve. The low-pressure liquid heat transfer medium then enters the indirect heat exchanger, the evaporator, in which the evaporated heat transfer medium absorbs heat. The heat transfer medium then returns to the compressor and the cycle is repeated.

Beside the transfer of waste heat from the water electrolysis to the purification of the raw methanol, the other process steps are conventional and known in the art.

In an embodiment of the invention, the distillation unit comprises two or more distillation towers operated in series.

In further an embodiment, at least a part of the water electrolyzed in the electrolysis unit is distillation water withdrawn from the methanol distillation unit.

The invention claimed is:

1. A process for the preparation of a methanol product comprising the steps of:
   a) providing a first process stream consisting essentially of carbon dioxide;
   b) providing a second process stream consisting of hydrogen by electrolyzing water in an electrolysis unit;
   c) mixing the first and second process stream in amount to obtain a methanol synthesis gas with a mole ratio of $H_2$ and $CO_2$ of between 2.5 and 3.5;
   d) catalytic converting the methanol synthesis gas into raw methanol in at least one methanol reactor;
   e) purifying the raw methanol in a distillation unit; and
   recovering waste heat generated in the electrolysis unit in step (b) by transferring the waste heat to a circulating heat transfer medium by indirect heat exchange with the waste heat and by indirect heat exchange of the heated heat transfer medium with steam used for the distillation of the raw methanol, wherein the heated transfer medium is compressed upstream the indirect heat exchange with steam.

2. Process of claim 1, wherein the heat transfer medium has a boiling point lower than the waste heat from the electrolysis at a pressure prevailing in the indirect heat exchange with the waste heat and a boiling point higher than the temperature in the indirect heat exchange with the steam at a pressure prevailing in the indirect heat exchange with the steam.

3. The process of claim 1, wherein the distillation unit comprises two or more distillation towers operated in series.

4. The process of claim 1, wherein at least a part of the water electrolyzed in the electrolysis unit is distillation water withdrawn from the methanol distillation unit.

* * * * *